(12) United States Patent
Berme et al.

(10) Patent No.: US 10,264,964 B1
(45) Date of Patent: Apr. 23, 2019

(54) EYE MOVEMENT MEASUREMENT DEVICE

(71) Applicant: Bertec Corporation, Columbus, OH (US)

(72) Inventors: Necip Berme, Worthington, OH (US); Jan Jakub Ober, Columbus, OH (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 16/022,061

(22) Filed: Jun. 28, 2018

Related U.S. Application Data (60) Provisional application No. 62/526,140, filed on Jun. 28, 2017.

(51) Int. Cl.
   *A61B 3/00* (2006.01)
   *A61B 3/14* (2006.01)
   (Continued)

(52) U.S. Cl.
   CPC ............ *A61B 3/113* (2013.01); *A61B 3/0008* (2013.01); *A61B 3/0025* (2013.01); *A61B 3/145* (2013.01); *A61B 3/18* (2013.01)

(58) Field of Classification Search
   CPC .......... A61B 3/113; A61B 2017/00694; A61B 3/1015; A61B 3/00; A61B 3/14; A61B 3/1005; A61B 3/102; A61B 3/103; A61B 3/107; A61B 3/117; A61B 5/103; A61B 2018/20359; A61B 2562/0219; A61B 3/0025; A61B 3/145; A61B 5/002; A61B 5/0022; A61B 5/0077; A61B 5/0496;
   (Continued)

(56) References Cited

U.S. PATENT DOCUMENTS

| | | |
|---|---|---|
| 6,038,488 A | 3/2000 | Barnes et al. |
| 6,113,237 A | 9/2000 | Ober et al. |

(Continued)

OTHER PUBLICATIONS

Eye Tracker with Scene Camera, SR Research Website, Web page <http://www.sr-research.com/EL_II_scam.html>, 1 page, dated Apr. 22, 2012, retrieved from Internet Archive Wayback Machine <https://web.archive.org/web/20120422195146/http://www.sr-research.com/EL_II_scam.html> on Oct. 15, 2014.

(Continued)

*Primary Examiner* — Brandi N Thomas
(74) *Attorney, Agent, or Firm* — The Law Office of Patrick F. O'Reilly III, LLC (57) ABSTRACT

An eye movement measurement device is disclosed herein. The eye movement measurement device includes at least one light source configured to illuminate one or more eyes of a user; at least one video-based sensor configured to detect low speed eye movements of the one or more eyes of the user and output one or more first signals based upon the detected low speed eye movements; at least one non-video-based sensor configured to detect high speed eye movements of the one or more eyes of the user and output one or more second signals based upon the detected high speed eye movements; and a data processing device operatively coupled to the light source, the video-based sensor, and the non-video-based sensor. The data processing device configured to calculate one or more eye movement output values for the one or more eyes of the user using the first and second signals.

20 Claims, 7 Drawing Sheets

(51) Int. Cl.
*A61B 3/113* (2006.01)
*A61B 3/18* (2006.01)

(58) Field of Classification Search
CPC ... A61B 5/1114; A61B 5/1118; A61B 5/4809;
A61B 5/6803; A61B 5/681; A61B 5/746;
A61F 2009/00846; A61F 2009/00872;
A61F 9/008; A61F 9/00804; A61F
2009/00897; A61F 2009/00857; A61F
2009/0088; A61F 9/00806; G02B
2027/014; G02B 27/0093; G02B 27/0101;
G02B 27/0172; G02B 2027/0178; G02B
2027/0138; G02B 2027/0141; G02B
2027/0187; G02B 2027/0194; G02B
27/0176; G02B 27/283; G02B 2027/0118;
G02B 2027/0134; G02B 2027/0167;
G02B 13/0095; G02B 17/0896
USPC ........ 351/200, 205, 206, 209–211, 221, 222,
351/243–246
See application file for complete search history.

(56) References Cited

U.S. PATENT DOCUMENTS

| | | | |
|---|---|---|---|
| 6,152,564 A | 11/2000 | Ober et al. | |
| 6,295,878 B1 | 10/2001 | Berme | |
| 6,354,155 B1 | 3/2002 | Berme | |
| 6,389,883 B1 | 5/2002 | Berme et al. | |
| 6,774,885 B1 | 8/2004 | Even-Zohar | |
| 6,936,016 B2 | 8/2005 | Berme et al. | |
| 8,181,541 B2 | 5/2012 | Berme | |
| 8,315,822 B2 | 11/2012 | Berme et al. | |
| 8,315,823 B2 | 11/2012 | Berme et al. | |
| D689,388 S | 9/2013 | Berme | |
| D689,389 S | 9/2013 | Berme | |
| 8,543,540 B1 | 9/2013 | Wilson et al. | |
| 8,544,347 B1 | 10/2013 | Berme | |
| 8,643,669 B1 | 2/2014 | Wilson et al. | |
| 8,700,569 B1 | 4/2014 | Wilson et al. | |
| 8,704,855 B1 | 4/2014 | Berme et al. | |
| 8,764,532 B1 | 7/2014 | Berme | |
| 8,847,989 B1 | 9/2014 | Berme et al. | |
| D715,669 S | 10/2014 | Berme | |
| 8,902,249 B1 | 12/2014 | Wilson et al. | |
| 8,915,149 B1 | 12/2014 | Berme | |
| 9,032,817 B2 | 5/2015 | Berme et al. | |
| 9,043,278 B1 | 5/2015 | Wilson et al. | |
| 9,066,667 B1 | 6/2015 | Berme et al. | |
| 9,081,436 B1 | 7/2015 | Berme et al. | |
| 9,168,420 B1 | 10/2015 | Berme et al. | |
| 9,173,596 B1 | 11/2015 | Berme et al. | |
| 9,200,897 B1 | 12/2015 | Wilson et al. | |
| 9,277,857 B1 | 3/2016 | Berme et al. | |
| D755,067 S | 5/2016 | Berme et al. | |
| 9,404,823 B1 | 8/2016 | Berme et al. | |
| 9,414,784 B1 | 8/2016 | Berme et al. | |
| 9,468,370 B1 | 10/2016 | Shearer | |
| 9,517,008 B1 | 12/2016 | Berme et al. | |
| 9,526,443 B1 | 12/2016 | Berme et al. | |
| 9,526,451 B1 | 12/2016 | Berme | |
| 9,558,399 B1 | 1/2017 | Jeka et al. | |
| 9,568,382 B1 | 2/2017 | Berme et al. | |
| 9,622,686 B1 | 4/2017 | Berme et al. | |
| 9,763,604 B1 | 9/2017 | Berme et al. | |
| 9,770,203 B1 | 9/2017 | Berme et al. | |
| 9,778,119 B2 | 10/2017 | Berme et al. | |
| 9,814,430 B1 | 11/2017 | Berme et al. | |
| 9,829,311 B1 | 11/2017 | Wilson et al. | |
| 9,854,997 B1 | 1/2018 | Berme et al. | |
| 9,916,011 B1 | 3/2018 | Berme et al. | |
| 9,927,312 B1 | 3/2018 | Berme et al. | |
| 10,010,248 B1 | 7/2018 | Shearer | |
| 10,010,286 B1 | 7/2018 | Berme et al. | |
| 2003/0216656 A1 | 11/2003 | Berme et al. | |
| 2008/0228110 A1 | 9/2008 | Berme | |
| 2011/0277562 A1 | 11/2011 | Berme | |
| 2012/0266648 A1 | 10/2012 | Berme et al. | |
| 2012/0271565 A1 | 10/2012 | Berme et al. | |
| 2015/0096387 A1 | 4/2015 | Berme et al. | |
| 2016/0080720 A1* | 3/2016 | Fullam | H04N 13/398 345/156 |
| 2016/0245711 A1 | 8/2016 | Berme et al. | |
| 2016/0334288 A1 | 11/2016 | Berme et al. | |
| 2016/0342206 A1* | 11/2016 | Shazly | A61B 5/1114 |
| 2018/0024015 A1 | 1/2018 | Berme et al. | |

OTHER PUBLICATIONS

Eye Gaze Tracking Under Natural Head Movements, Zhiwei Zhu and Qiang Ji, 2005 IEEE.

Efficient real-time algorithms for eye state and head pose tracking in Advanced Driver Support Systems, Riad L. Hammoud, Andrew Wilhelm, Phillip Malawey, and Gerald J. Witt, 2005, IEEE.

Combined Head and Eye Tracking System for Dynamic Testing of the Vestibular System, Robert S. Allison, Moshe Eizenman, and Bob S. K. Cheung, IEEE Transactions on Biomedical Engineering, vol. 41, No. 11, Nov. 1996.

Active Eye-Tracking System by Using Quad PTZ Cameras, Chao-Ning Chan, Shunichiro Oe, Chem-Sheng Lint, IEEE 2007.

A Cascaded Scheme for Eye Tracking and Head Movement Compensation, X. Xie, R. Sudhakar, H. Zhuang, Systems and Humans, vol. 28, No. 4, Jul. 1998.

* cited by examiner

EYE MOVEMENT MEASUREMENT DEVICE

CROSS-REFERENCE TO RELATED APPLICATIONS

This patent application claims priority to, and incorporates by reference in its entirety, U.S. Provisional Patent Application No. 62/526,140, entitled "Eye Movement Measurement Device", filed on Jun. 28, 2017.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to an eye movement measurement device. More particularly, the invention relates to an eye movement measurement device that is capable of effectively measuring both high and low speed eye movements.

2. Background

The widely used conventional method for the measurement of eye movements is the scleral search coil (SSC) method. This method involves inserting contact lenses embedded with coils on the cornea and measuring the electromagnetic signals induced in the coils.

The SSC method provides very accurate measurements of both low-speed and high-speed eye movements in three dimensions. However, the method is not suitable for routine clinical testing because of its invasiveness and because of its relatively long preparation time.

Today for clinical testing, video recording and analysis of pupil movements is the method of choice. The method is non-invasive, but high-speed cameras are exponentially more expensive. Therefore, most cameras in the video-based clinical eye movement measurement systems are limited to 250 Hz.

An alternative method is using a non-video based infrared technology that can provide much higher speeds (approximately 2,000 Hz or more). However, these systems also have limitations. For example, there is electronic drift and measuring eye movements in complete darkness is difficult and not as accurate.

What is needed, therefore, is a non-invasive eye movement measurement device that is capable of accurately measuring of both low-speed and high-speed eye movements in a clinical setting. Moreover, an eye movement measurement device is needed that enables both low-speed and high-speed eye movements to be accurately measured without requiring a long preparation time. Furthermore, a need exists for an eye movement measurement device that utilizes hybrid technology so as to minimize the limitations associated with conventional devices relying upon a single type of measurement means.

BRIEF SUMMARY OF EMBODIMENTS OF THE INVENTION

Accordingly, the present invention is directed to an eye movement measurement device that substantially obviates one or more problems resulting from the limitations and deficiencies of the related art.

In accordance with one or more embodiments of the present invention, there is provided an eye movement measurement device that includes at least one light source configured to illuminate one or more eyes of a user; at least one video-based sensor configured to detect low speed eye movements of the one or more eyes of the user and output one or more first signals based upon the detected low speed eye movements; at least one non-video-based sensor configured to detect high speed eye movements of the one or more eyes of the user and output one or more second signals based upon the detected high speed eye movements; and a data processing device operatively coupled to the at least one light source, the at least one video-based sensor, and the at least one non-video-based sensor, the data processing device configured to receive the one or more first signals that are generated based upon the detected low speed eye movements and the one or more second signals that are generated based upon the detected high speed eye movements, and to calculate one or more eye movement output values for the one or more eyes of the user based upon the one or more first signals and the one or more second signals.

In a further embodiment of the present invention, the at least one light source comprises one or more light emitting diodes configured to illuminate the one or more eyes of the user, wherein the data processing device is configured to activate the one or more light emitting diodes prior to detection of the low speed eye movements by the at least one video-based sensor or prior to detection of the high speed eye movements by the at least one non-video-based sensor.

In yet a further embodiment, the at least one video-based sensor comprises one or more video cameras.

In still a further embodiment, the at least one non-video-based sensor is selected from the group consisting of an infrared sensor, an ultrasound sensor, an electooculographic sensor, and combinations thereof.

In yet a further embodiment, the eye movement measurement device further comprises a dichroic mirror disposed in a path of a reflected image of one of the one or more eyes of the user between the one of the one or more eyes of the user and the at least one video-based sensor.

In still a further embodiment, the eye movement measurement device further comprises a head position detection device, the head position detection device configured to detect a position of the head of the user and output one or more third signals that are representative of the detected position of the head of the user.

In yet a further embodiment, the head position detection device comprises one or more inertial measurement units.

In still a further embodiment, the eye movement measurement device further comprises a support frame on which the at least one light source, the at least one video-based sensor, and the at least one non-video-based sensor are mounted, the support frame configured to be worn on the head of the user.

In yet a further embodiment, the support frame is in the form of a pair of goggles.

In still a further embodiment, the eye movement measurement device further comprises a frame slippage detection device, the frame slippage detection device configured to detect a slippage of the support frame relative to the head of the user.

In yet a further embodiment, the frame slippage detection device comprises one or more video cameras.

In still a further embodiment, the eye movement measurement device further comprises a light-proof cover mounted on the support frame, the light-proof cover configured to at least partially surround a front of the support frame so as to permit the eye movements of the user to be detected in darkness.

In yet a further embodiment, the eye movement measurement device further comprises a target generation device mounted on the support frame, the target generation device configured to generate a target and project the target onto a surface in front of the user such that the target is visible by the one or more eyes of the user.

In still a further embodiment, the target generation device is in the form of a laser light source or a light emitting diode.

In yet a further embodiment, the eye movement measurement device further comprises a data storage device mounted on the support frame, the data storage device comprising non-volatile data storage means, and the data storage device configured to store eye movement data from the data processing device so as to enable the eye movement data to be subsequently downloaded to a remote computing device.

In still a further embodiment, the data processing device is operatively coupled to the at least one video-based sensor and the at least one non-video-based sensor by means of a hardwired connection or a wireless connection.

In accordance with one or more other embodiments of the present invention, there is provided an eye movement measurement device that includes a support frame configured to be worn on the head of a user; at least one light source mounted on the support frame, the at least one light source configured to illuminate one or more eyes of the user; at least one video-based sensor mounted on the support frame, the at least one video-based sensor configured to detect low speed eye movements of the one or more eyes of the user and output one or more first signals based upon the detected low speed eye movements; at least one non-video-based sensor mounted on the support frame, the at least one non-video-based sensor configured to detect high speed eye movements of the one or more eyes of the user and output one or more second signals based upon the detected high speed eye movements; a head position detection device, the head position detection device configured to detect a position of the head of the user and output one or more third signals that are representative of the detected position of the head of the user; and a data processing device operatively coupled to the at least one light source, the at least one video-based sensor, the at least one non-video-based sensor, and the head position detection device, the data processing device configured to receive the one or more first signals that are generated based upon the detected low speed eye movements, the one or more second signals that are generated based upon the detected high speed eye movements, and the one or more third signals that are generated based upon the detected position of the head of the user, and the data processing device configured to determine one or more gaze directions of the user from the one or more first signals output by the at least one video-based sensor, the one or more second signals output by the at least one non-video-based sensor, and the one or more third signals output by the head position detection device.

In a further embodiment of the present invention, the at least one light source comprises one or more light emitting diodes configured to illuminate the one or more eyes of the user, wherein the data processing device is configured to activate the one or more light emitting diodes prior to detection of the low speed eye movements by the at least one video-based sensor or prior to detection of the high speed eye movements by the at least one non-video-based sensor.

In yet a further embodiment, the at least one video-based sensor comprises one or more video cameras.

In still a further embodiment, the at least one non-video-based sensor is selected from the group consisting of an infrared sensor, an ultrasound sensor, an electooculographic sensor, and combinations thereof.

In yet a further embodiment, the eye movement measurement device further comprises a dichroic mirror disposed in a path of a reflected image of one of the one or more eyes of the user between the one of the one or more eyes of the user and the at least one video-based sensor.

In still a further embodiment, the head position detection device comprises one or more inertial measurement units.

In yet a further embodiment, the support frame is in the form of a pair of goggles.

In still a further embodiment, the eye movement measurement device further comprises a frame slippage detection device, the frame slippage detection device configured to detect a slippage of the support frame relative to the head of the user.

In yet a further embodiment, the frame slippage detection device comprises one or more video cameras.

In still a further embodiment, the eye movement measurement device further comprises a light-proof cover mounted on the support frame, the light-proof cover configured to at least partially surround a front of the support frame so as to permit the eye movements of the user to be detected in darkness.

In yet a further embodiment, the eye movement measurement device further comprises a target generation device mounted on the support frame, the target generation device configured to generate a target and project the target onto a surface in front of the user such that the target is visible by the one or more eyes of a user.

In still a further embodiment, the target generation device is in the form of a laser light source or a light emitting diode.

In yet a further embodiment, the eye movement measurement device further comprises a data storage device mounted on the support frame, the data storage device comprising non-volatile data storage means, and the data storage device configured to store eye movement data from the data processing device so as to enable the eye movement data to be subsequently downloaded to a remote computing device.

In still a further embodiment, the data processing device is operatively coupled to the at least one video-based sensor and the at least one non-video-based sensor by means of a hardwired connection or a wireless connection.

It is to be understood that the foregoing summary and the following detailed description of the present invention are merely exemplary and explanatory in nature. As such, the foregoing summary and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

Figure 1:
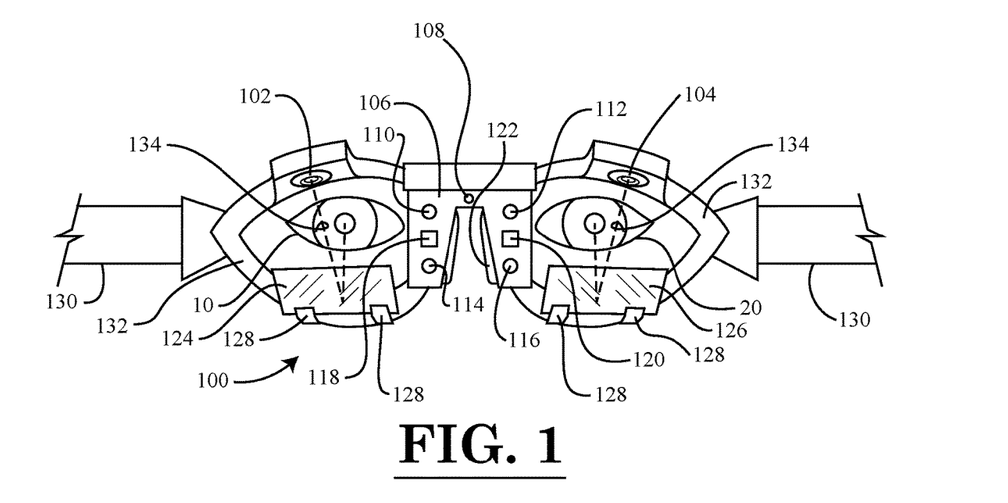
FIG. 1 is a front view of an eye movement measurement device, according to a first embodiment of the invention.
Figure 2:
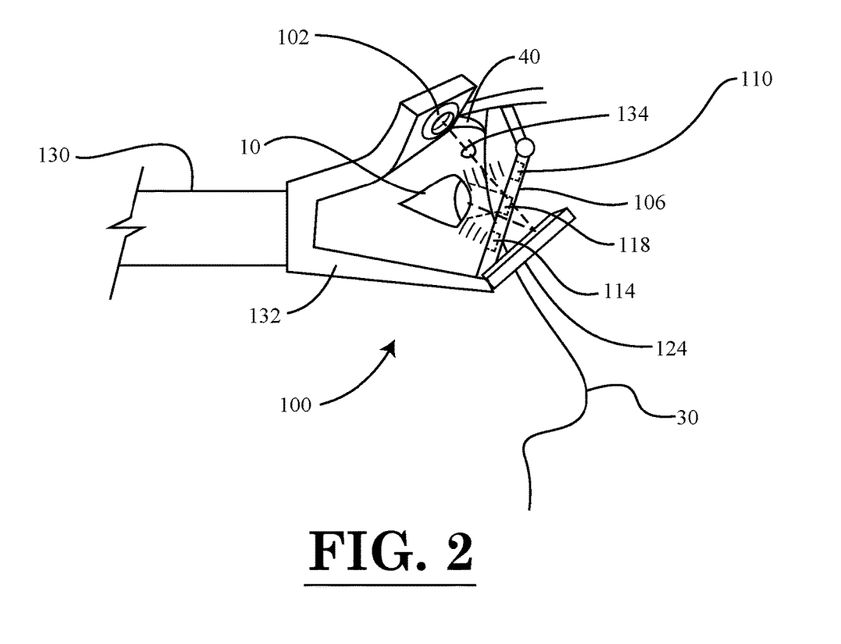
FIG. 2 is a right side view of the eye movement measurement device of FIG. 1.
Figure 7:
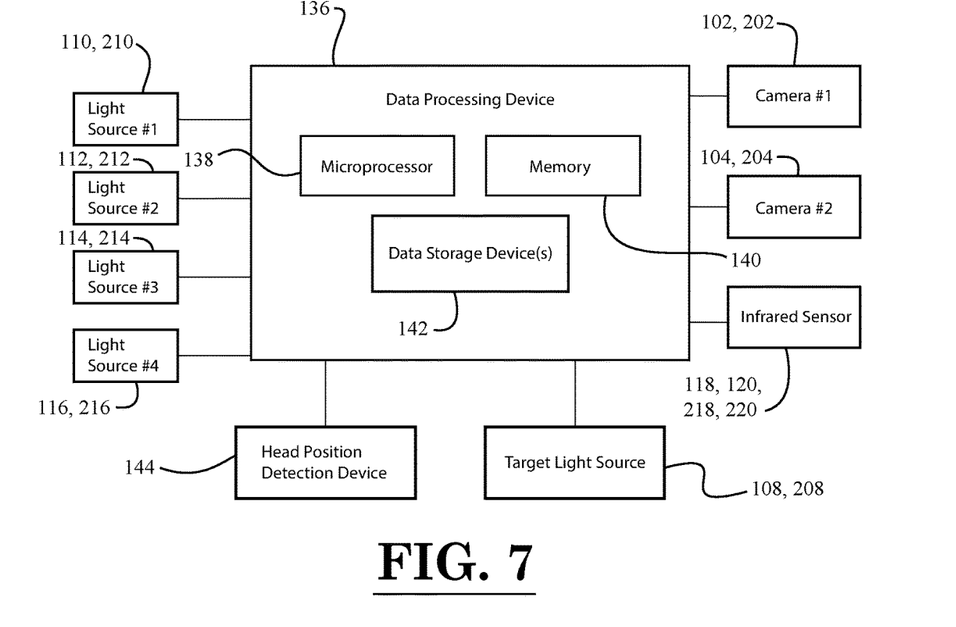
FIG. 7 is a block diagram of constituent components of the eye movement measurement devices of FIGS. 1 and 3.

A first illustrative embodiment of an eye movement measurement device is seen generally at 100 in FIGS. 1, 2, and 7. As shown in FIGS. 1, 2, and 7, the eye movement measurement device 100 of the first illustrative embodiment generally comprises a support frame 132 configured to be worn on the head of a user; a plurality of light sources 110, 112, 114, 116 mounted on the central support structure 106 of the support frame 132, the plurality of light sources 110, 112, 114, 116 configured to illuminate the eyes 10, 20 of the user; a pair of video-based sensors 102, 104 mounted on the support frame 132, the pair of video-based sensors 102, 104 configured to detect low speed eye movements of the eyes 10, 20 of the user and output a plurality of first signals based upon the detected low speed eye movements; a pair of non-video-based sensors 118, 120 mounted on the central support structure 106 of the support frame 132, the pair of non-video-based sensors 118, 120 configured to detect high speed eye movements of the one or more eyes of the user and output a plurality of second signals based upon the detected high speed eye movements; a head position detection device 144 (see FIG. 7), the head position detection device 144 configured to detect a position of the head of the user and output one or more third signals that are representative of the detected position of the head of the user; and a data processing device 136 (see FIG. 7) operatively coupled to the plurality of light sources 110, 112, 114, 116, the pair of video-based sensors 102, 104, the pair of non-video-based sensors 118, 120, and the head position detection device 144, the data processing device 136 configured to receive the plurality of first signals that are generated based upon the detected low speed eye movements, the plurality of second signals that are generated based upon the detected high speed eye movements, and the one or more third signals that are generated based upon the detected position of the head of the user, and the data processing device 136 configured to determine one or more gaze directions of the user from the plurality of first signals output by the pair of video-based sensors 102, 104, the plurality of second signals output by the pair of non-video-based sensors 118, 120, and the one or more third signals output by the head position detection device 144.

In the illustrative embodiment, the eye movement output values are given in terms of degrees of displacement. The center gaze is labeled as 0 degrees. Horizontal and vertical deviations of a line that projects out of the center of pupil from the center gaze, measured in degrees, represent the horizontal and vertical eye movements. Prior to data collection, a calibration is necessary to convert the measured parameters into actual eye movements.

In the illustrative embodiment, the calibration process involves asking the user to look back and forth among two or more pre-specified dots placed in front of the user that generate known eye angles. The values derived during the calibration process are then used to convert the measured parameters into eye movements.

Now, with reference again to FIGS. 1, 2, and 7, the plurality of light sources 110, 112, 114, 116 of the eye movement measurement device 100 will be described. As shown in the front and side views of FIGS. 1 and 2, in the illustrative embodiment, each of the plurality of light sources 110, 112, 114, 116 comprises one or more light emitting diodes (LEDs) configured to illuminate the one or more eyes of the user. The data processing device 136 is configured to activate the one or more light emitting diodes prior to detection of the low speed eye movements by the pair of video-based sensors 102, 104 and prior to detection of the high speed eye movements by the non-video-based sensors 118, 120. The light emitting diodes remain on during the entirety of the eye movement testing to illuminate the eyes of the user. In the illustrative embodiment, the plurality of light emitting diodes may be in form of infrared light emitting diodes.

Referring to FIGS. 1 and 2, the pair of video-based sensors 102, 104 of the eye movement measurement device 100 will be explained. In the illustrative embodiment, each of the pair of video-based sensors 102, 104 comprises a video camera mounted proximate to a respective eyebrow 40 of the user. In one exemplary embodiment, the pair of video cameras may comprise a pair of infrared cameras. Although, in an alternative embodiment, rather than being in the form of infrared cameras, the video cameras may be in the form of black-and-white cameras or color cameras. In the illustrative embodiment, each of the video cameras is in the form of a high-speed camera (e.g., a 250 Hz camera or other suitable high-speed camera). Also, in the illustrative embodiment, the video-based sensors 102, 104 measure low-speed eye movements, which are eye movements less than or equal to 100 degrees per second.

Next, the pair of non-video-based sensors 118, 120 will be described with reference to FIGS. 1 and 2. In the illustrative embodiment, the non-video-based sensors 118, 120 utilize direct infrared illumination and sensing means (see FIGS. 1 and 2). In the illustrative embodiment, the nasal portion of both eyes 10, 20 of the user is illuminated by infrared light and the infrared sensors 118, 120 are used to measure the amount of reflected infrared light (as shown in the diagrammatic view of FIG. 6). For example, as the corneal bulge (i.e., the protruding spherical cornea) of the eyes 10, 20 of the user moves away from the light sources 110, 112, 114, 116, less light is reflected to the infrared light detectors 118, 120, which may be in the form of photodiodes or other types of sensors for detecting infrared light. In the illustrative embodiment, the illuminators 110, 112, 114, 116 and sensors 118, 120 may be attached to the nose bridge component 122 of the head-mounted support frame 132 by means of the central support structure 106. The measurement principle of the illustrative non-video-based sensors 118, 120 is based on taking the differences between the averages of reflected light from the areas of the eyes 10, 20 near the nose 30 of the user. In the illustrative embodiment, the non-video-based sensors 118, 120 measure high-speed eye movements, which are eye movements greater than 100 degrees per second. In the illustrative embodiment, the sampling rate of the non-video-based sensors 118, 120 may be 1,000 Hz or more. In other embodiments, rather than using direct infrared illumination and sensing means for the non-video-based sensors 118, 120, the non-video-based sensors may be in the form of ultrasound sensors, electooculographic sensors, and combinations thereof.

In the illustrative embodiment, the data from the video-based sensors 102, 104 and the non-video-based sensors 118, 120 is collected in parallel. The video-based sensors 102, 104 track the centers of the pupils and convert them to eye movements. The non-video-based sensors 118, 120 track the curvature of the cornea and convert it to eye movements. Using the time stamps from both the video-based sensors 102, 104 and the non-video-based sensors 118, 120, the eye movement data from the sensors 102, 104, 118, 120 is synchronized. The measured values from the video sensors 102, 104 are used to correct for the drift of the non-video tracings. Conversely, the measured values from the non-video sensors 118, 120 are used to add samples to the tracings from the video sources. The combined tracings derived from this process can accurately represent both slow and fast eye movements.

As mentioned above, in the illustrative embodiment, the measurements from both the video-based and non-video-based sensors 102, 104, 118, 120 are eventually converted to represent eye movements in degrees. The time stamps from both sets of sensors 102, 104, 118, 120 are used to synchronize the recordings. The video-based sensors 102, 104 have a better low-frequency performance, which is used to correct for drift of the non-video-based sensors 118, 120. The non-video-based sensors 118, 120 have a better high-frequency performance, which is used to increase the number of sampling points during fast eye movements. In addition, after the data processing, eye velocities in degrees per second are eventually calculated. At the same time, the head velocities can be measured using a head position detection device 144, which may be in the form of an inertial measurement unit (IMU) embedded in the support frame 132 worn by the user. The performance of the vestibulo-ocular reflex (VOR) is quantified by comparing the head velocity versus the eye velocities. The ratio of slow eye velocities (VOR eye movements) to head velocities, as well as the number and velocity of fast eye movements (saccades) are used to quantify the subject/user performance.

Figure 6:
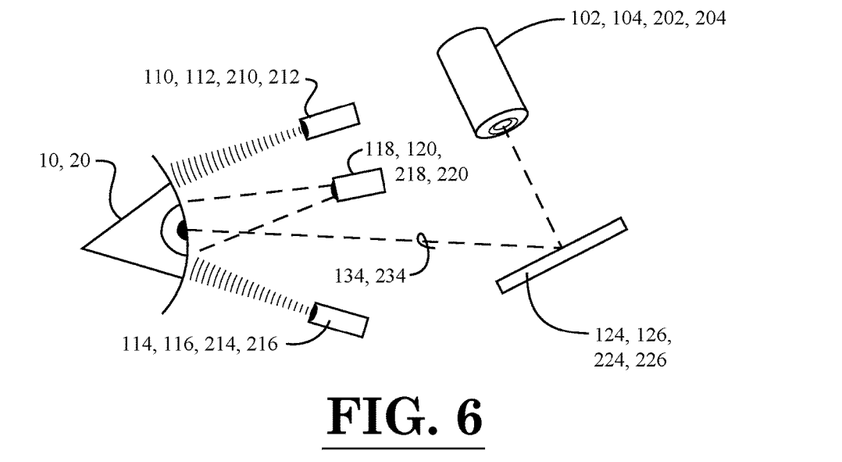
FIG. 6 is a schematic diagram illustrating the functionality of the video-based sensors and the non-video-based sensors of the eye movement measurement devices of FIGS. 1 and 3.

As shown in FIGS. 1 and 2, the eye movement measurement device 100 further includes a pair of dichroic mirrors 124, 126 mounted to the lower portion of the support frame 132. Each of the dichroic mirrors 124, 126 is secured to the lower portion of the support frame 132 by a respective pair of spaced-apart mounting brackets 128. In the first illustrative embodiment, it can be seen that the field of view of the user is substantially unobstructed by the dichroic mirrors 124, 126 because the mirrors 124, 126 are positioned below the eyes 10, 20 of the user. In the schematic diagram of FIG. 6, it can be seen each dichroic mirror 124, 126 is disposed in the path 134 of the reflected eye image between the eye 10, 20 and the respective camera 102, 104. As shown in FIG. 6, the image of the eye 10, 20 is reflected off the dichroic mirror 124, 126, and captured by the lens of the camera 102, 104.

Turning to FIG. 7, the head position detection device 144 of the eye movement measurement device 100 will be explained. In the illustrated embodiment, the head position detection device 144 is mounted on the support frame 132 that contains the pair of video-based sensors 102, 104 and the pair of non-video-based sensors 118, 120. The head position detection device 144 may be in the form of an inertial measurement unit (IMU) mounted on the support frame 132 worn by the user.

In the illustrative embodiment, it can be seen that the head-mounted support frame 132 of the eye movement measurement device 100 is in the form of an eyeglass frame worn by the user. In one or more other embodiments, the head-mounted support frame 132 may be in the form of a pair of goggles worn by the user. As shown in FIGS. 1 and 2, a head strap 130 is attached to the opposed sides of the support frame 132 for attaching the eye movement measurement device 100 to the head of the user. In the illustrative embodiment, the head strap 130 is resilient so that it is capable of being stretched to accommodate the head size of the user, and then, fitted in place on the head of the user. The head strap 130 can be formed from any suitable stretchable fabric, such as neoprene, spandex, and elastane. Alternatively, the head strap 130 could be formed from a generally non-stretchable fabric, and be provided with latching means or clasp means for allowing the head strap 130 to be split into two portions (e.g., the head strap 130 could be provided with a snap-type latching device).

In one or more further embodiments, eye movement measurement device 100 may additionally comprise a frame slippage detection device that is configured to detect a slippage of the support frame 132 relative to the head of the user. In the one or more further embodiments, the frame slippage detection device may be in the form of one or more externally disposed video cameras that are used to detect the slippage of the support frame 132. In the illustrative embodiment, the frame slippage detection device is in the form of a stationary camera disposed in front of the eye movement measurement device 100 for detecting the slippage of the support frame 132.

Also, in one or more further embodiments, the eye movement measurement device 100 may additionally comprise a light-proof cover mounted on the support frame 132.

The light-proof cover is configured to at least partially surround a front of the support frame 132 so as to permit the eye movements of the user to be detected in darkness. As such, the light-proof cover enables the eye movements of the user to be recorded in complete darkness or nearly complete darkness. In one or more embodiments, the light-proof cover is in the form of a pull-down visor, such as that used on welding goggles. In one or more alternative embodiments, light-proof cover is in the form of a snap-on cover that snaps around the support frame 132, and in front of the dichroic mirrors 124, 126.

Referring again to FIG. 1, it can be seen that, in the illustrative embodiment, the eye movement measurement device 100 further comprises a target generation device (e.g., a target light source 108) mounted on the support frame 132. The target generation device 108 is configured to generate a target and project the target onto a surface (e.g., a wall surface) in front of the user such that the target is visible by the eyes 10, 20 of the user. The target generation device 108 may be in the form of a laser light source or a light emitting diode.

In addition, in one or more embodiments, the eye movement measurement device 100 further comprises a data storage device mounted on the support frame 132. The data storage device comprises non-volatile data storage means, and is configured to store eye movement data so as to enable the eye movement data to be subsequently downloaded to a remote computing device.

Now, turning to FIG. 7, it can be seen that the illustrated data acquisition/data processing device 136 (e.g., a computing device) of the eye movement measurement device 100 includes a microprocessor 138 for processing data, memory 140 (e.g., random access memory or RAM) for storing data during the processing thereof, and data storage device(s) 142, such as one or more hard drives, compact disk drives, floppy disk drives, flash drives, or any combination thereof. As shown in FIG. 7, the light sources 110, 112, 114, 116, the pair of video-based sensors 102, 104, and the pair of non-video-based sensors 118, 120 are operatively coupled to the data acquisition/data processing device 136. Also, as illustrated in FIG. 7, the target light source 108 and the head position detection device 144 are operatively coupled to the data acquisition/data processing device 136. In some embodiments, the data acquisition/data processing device 136 can be in the form of a desktop computer or laptop computer remotely located from the support frame 132 of the eye movement measurement device 100, while in other embodiments, the data acquisition/data processing device 136 can be embodied as a mini-computer mounted on the support frame 132.

In the illustrative embodiment, the data processing device 136 is operatively coupled to the light sources 110, 112, 114, 116, the pair of video-based sensors 102, 104, the pair of non-video-based sensors 118, 120, the target light source 108 and the head position detection device 144 by means of a wireless connection. In an alternative embodiment, the data processing device 136 may be operatively coupled to the light sources 110, 112, 114, 116, the pair of video-based sensors 102, 104, the pair of non-video-based sensors 118, 120, the target light source 108 and the head position detection device 144 by means of a hardwired connection.

Figure 3:
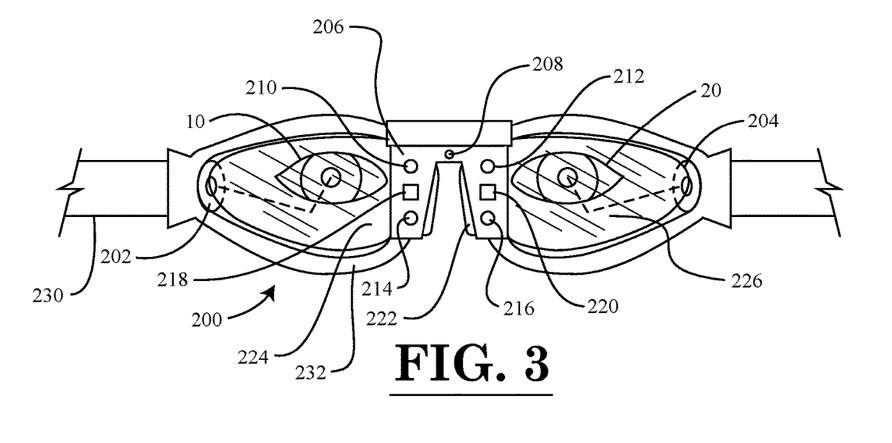
FIG. 3 is a front view of an eye movement measurement device, according to a second embodiment of the invention.
Figure 4:
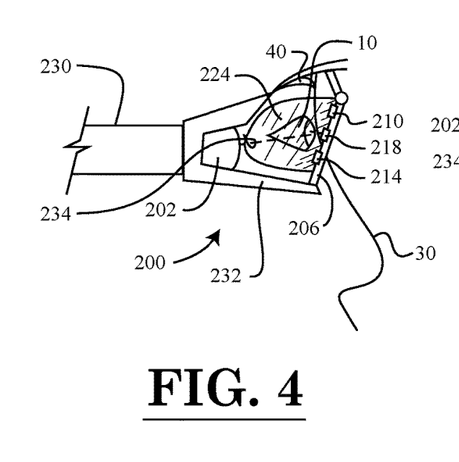
FIG. 4 is a right side view of the eye movement measurement device of FIG. 3.
Figure 5:
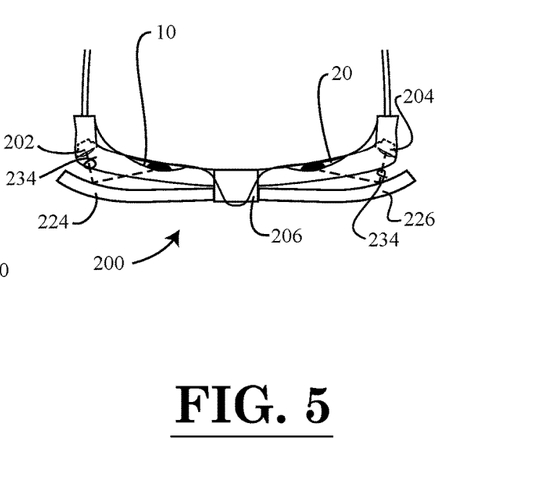
FIG. 5 is a top view of the eye movement measurement device of FIG. 3.

FIGS. 3-5 illustrate an eye movement measurement device 200 according to a second illustrative embodiment of the present invention. With reference to these figures, it can be seen that, in many respects, the second illustrative embodiment is similar to that of the first embodiment. Moreover, some parts are common to both such embodiments. For the sake of brevity, the elements that the second embodiment of the eye movement measurement device has in common with the first embodiment will only be briefly mentioned, if at all, because these components have already been explained in detail above Initially, referring collectively to FIGS. 3-5 and 7, it can be seen that, like the first illustrative embodiment, the eye movement measurement device 200 of the second illustrative embodiment generally comprises a support frame 232 configured to be worn on the head of a user; a plurality of light sources 210, 212, 214, 216 mounted on the central support structure 206 of the support frame 232, the plurality of light sources 210, 212, 214, 216 configured to illuminate the eyes 10, 20 of the user; a pair of video-based sensors 202, 204 mounted on the support frame 232, the pair of video-based sensors 202, 204 configured to detect low speed eye movements of the eyes 10, 20 of the user and output a plurality of first signals based upon the detected low speed eye movements; a pair of non-video-based sensors 218, 220 mounted on the central support structure 206 of the support frame 232, the pair of non-video-based sensors 218, 220 configured to detect high speed eye movements of the one or more eyes of the user and output a plurality of second signals based upon the detected high speed eye movements; a head position detection device 144 (see FIG. 7), the head position detection device 144 configured to detect a position of the head of the user and output one or more third signals that are representative of the detected position of the head of the user; and a data processing device 136 (see FIG. 7) operatively coupled to the plurality of light sources 210, 212, 214, 216, the pair of video-based sensors 202, 204, the pair of non-video-based sensors 218, 220, and the head position detection device 144, the data processing device 136 configured to receive the plurality of first signals that are generated based upon the detected low speed eye movements, the plurality of second signals that are generated based upon the detected high speed eye movements, and the one or more third signals that are generated based upon the detected position of the head of the user, and the data processing device 136 configured to determine one or more gaze directions of the user from the plurality of first signals output by the pair of video-based sensors 202, 204, the plurality of second signals output by the pair of non-video-based sensors 218, 220, and the one or more third signals output by the head position detection device 144.

As explained above for the first illustrative embodiment, the eye movement output values are given in terms of degrees of displacement. The center gaze is labeled as 0 degrees. Horizontal and vertical deviations of a line that projects out of the center of pupil from the center gaze, measured in degrees, represent the horizontal and vertical eye movements.

Now, with reference again to FIGS. 3-5 and 7, the plurality of light sources 210, 212, 214, 216 of the eye movement measurement device 200 will be described. As shown in the front and side views of FIGS. 3 and 4, in the illustrative embodiment, each of the plurality of light sources 210, 212, 214, 216 comprises one or more light emitting diodes (LEDs) configured to illuminate the one or more eyes of the user. The data processing device 136 is configured to activate the one or more light emitting diodes prior to detection of the low speed eye movements by the pair of video-based sensors 202, 204 and prior to detection of the high speed eye movements by the non-video-based sensors 218, 220. The light emitting diodes remain on during the entirety of the eye movement testing to illuminate the eyes of the user. As described above for the first embodiment, in the illustrative embodiment, the plurality of light emitting diodes may be in form of infrared light emitting diodes.

Referring to FIGS. 3 and 4, the pair of video-based sensors 202, 204 of the eye movement measurement device 200 will be explained. In the illustrative embodiment, each of the pair of video-based sensors 202, 204 comprises a video camera mounted proximate to a respective temple of the user (i.e., each video camera 202, 204 is disposed outwardly from a respective eye of the user—see FIG. 3). In one exemplary embodiment, the pair of video cameras may comprise a pair of infrared cameras. Although, in an alternative embodiment, rather than being in the form of infrared cameras, the video cameras may be in the form of black-and-white cameras or color cameras. In the illustrative embodiment, each of the video cameras is in the form of a high-speed camera (e.g., a 250 Hz camera or other suitable high-speed camera). Also, in the illustrative embodiment, the video-based sensors 202, 204 measure low-speed eye movements, which are eye movements less than or equal to 100 degrees per second.

Next, the pair of non-video-based sensors 218, 220 will be described with reference to FIGS. 3 and 4. In the illustrative embodiment, the non-video-based sensors 218, 220 utilize direct infrared illumination and sensing means (see FIGS. 3 and 4). In the illustrative embodiment, the nasal portion of both eyes 10, 20 of the user is illuminated by infrared light and the infrared sensors 218, 220 are used to measure the amount of reflected infrared light (as shown in the diagrammatic view of FIG. 6). For example, as the corneal bulge (i.e., the protruding spherical cornea) of the eyes 10, 20 of the user moves away from the light sources 210, 212, 214, 216, less light is reflected to the infrared light detectors 218, 220, which may be in the form of photodiodes or other types of sensors for detecting infrared light. In the illustrative embodiment, the illuminators 210, 212, 214, 216 and sensors 218, 220 may be attached to the nose bridge component 222 of the head-mounted support frame 232 by means of the central support structure 206. The measurement principle of the illustrative non-video-based sensors 218, 220 is based on taking the differences between the averages of reflected light from the areas of the eyes 10, 20 near the nose 30 of the user. In the illustrative embodiment, the non-video-based sensors 218, 220 measure high-speed eye movements, which are eye movements greater than 100 degrees per second. In other embodiments, rather than using direct infrared illumination and sensing means for the non-video-based sensors 218, 220, the non-video-based sensors may be in the form of ultrasound sensors, electooculographic sensors, and combinations thereof.

As described above for the first illustrative embodiment, the data from the video-based sensors 202, 204 and the non-video-based sensors 218, 220 is collected in parallel. The video-based sensors 202, 204 track the centers of the pupils and convert them to eye movements. The non-video-based sensors 218, 220 track the curvature of the cornea and convert it to eye movements. Using the time stamps from both the video-based sensors 202, 204 and the non-video-based sensors 218, 220, the eye movement data from the sensors 202, 204, 218, 220 is synchronized. The measured values from the video sensors 202, 204 are used to correct for the drift of the non-video tracings. Conversely, the measured values from the non-video sensors 218, 220 are used to add samples to the tracings from the video sources. The combined tracings derived from this process can accurately represent both slow and fast eye movements.

As mentioned above, in the illustrative embodiment, the measurements from both the video-based and non-video-based sensors 202, 204, 218, 220 are eventually converted to represent eye movements in degrees. The time stamps from both sets of sensors 202, 204, 218, 220 are used to synchronize the recordings. The video-based sensors 202, 204 have a better low-frequency performance, which is used to correct for drift of the non-video-based sensors 218, 220. That is, the output data from the video-based sensors 202, 204 may be used to determine the amount by which the sampling curve produced by the non-video-based sensors 218, 220 is shifted or offset due to the effects of sensor drift. The non-video-based sensors 218, 220 have a better high-frequency performance, which is used to increase the number of sampling points during fast eye movements. That is, the additional sampling points generated by the non-video-based sensors 218, 220 may be used to fill-in sampling points between the sampling points generated using the video-based sensors 202, 204 by using an interpolation algorithm, etc. (e.g., a quadratic interpolation algorithm). For example, the equation provided below may be used to align the curves generated by the video-based sensors 202, 204 and the non-video-based sensors 218, 220 so that the drift and additional sampling point corrections may be applied:

$$\vec{N} = a \cdot I \cdot \vec{S} + b \quad (1)$$

where:

$\vec{N}$: interpolated values for a series of time points obtained from the video-based sensor(s);

I: identity matrix; and $\vec{S}$: sensed values for the same time points obtained from the non-video-based sensors.

In addition to applying the drift and additional sampling point corrections, in the illustrative embodiment, a cross-correlation technique may also be applied so as to correct for an unknown time shift due to an unknown latency in the video output data generated by the video-based sensors 202, 204 (i.e., cameras). In addition, after the data processing, eye velocities in degrees per second are eventually calculated. At the same time, the head velocities can be measured using the head position detection device 144, which may be in the form of an inertial measurement unit (IMU) embedded in the support frame 232 worn by the user. The performance of the vestibulo-ocular reflex (VOR) is quantified by comparing the head velocity versus the eye velocities. The ratio of slow eye velocities (VOR eye movements) to head velocities, as well as the number and velocity of fast eye movements (saccades) are used to quantify the subject/user performance.

As shown in FIGS. 3-5, the eye movement measurement device 200 further includes a pair of dichroic mirrors 224, 226 mounted to the central support structure 206 of the support frame 232. In the second illustrative embodiment, it can be seen that the dichroic mirrors 224, 226 are disposed in front of the eyes 10, 20 of the user so as to generally cover the field of view of the user, rather than being positioned below the eyes 10, 20 of the user, as in the first illustrative embodiment. Each of the dichroic mirrors 224, 226 is configured so as to reflect the eye image back to the camera 202, 204, yet still allow the user to see through the mirror 224, 226 so that the surrounding environment is visible to him or her. Particularly, in the schematic diagram of FIG. 6, it can be seen each dichroic mirror 224, 226 is disposed in the path 234 of the reflected eye image between the eye 10, 20 and the respective camera 202, 204. As shown in FIG. 6, the image of the eye 10, 20 is reflected off the dichroic mirror 224, 226, and captured by the lens of the camera 202, 204.

Turning to FIG. 7, the head position detection device 144 of the eye movement measurement device 200 will be explained. Similar to that described above for the first illustrative embodiment, the head position detection device 144 is mounted on the support frame 232 that contains the pair of video-based sensors 202, 204 and the pair of non-video-based sensors 218, 220. The head position detection device 144 may be in the form of an inertial measurement unit (IMU) mounted on the support frame 232 worn by the user.

In the illustrative embodiment, it can be seen that the head-mounted support frame 232 of the eye movement measurement device 200 is in the form of an eyeglass frame worn by the user. In one or more other embodiments, the head-mounted support frame 232 may be in the form of a pair of goggles worn by the user. As shown in FIGS. 3 and 4, a head strap 230 is attached to the opposed sides of the support frame 232 for attaching the eye movement measurement device 200 to the head of the user. In the illustrative embodiment, the head strap 230 is resilient so that it is capable of being stretched to accommodate the head size of the user, and then, fitted in place on the head of the user. The head strap 230 can be formed from any suitable stretchable fabric, such as neoprene, spandex, and elastane. Alternatively, the head strap 230 could be formed from a generally non-stretchable fabric, and be provided with latching means or clasp means for allowing the head strap 230 to be split into two portions (e.g., the head strap 230 could be provided with a snap-type latching device).

In one or more further embodiments, eye movement measurement device 200 may additionally comprise a frame slippage detection device that is configured to detect a slippage of the support frame 232 relative to the head of the user. In the one or more further embodiments, the frame slippage detection device may be in the form of one or more externally disposed video cameras that are used to detect the slippage of the support frame 232. In the illustrative embodiment, the frame slippage detection device is in the form of a stationary camera disposed in front of the eye movement measurement device 200 for detecting the slippage of the support frame 232.

Also, in one or more further embodiments, the eye movement measurement device 200 may additionally comprise a light-proof cover mounted on the support frame 232. The light-proof cover is configured to at least partially surround a front of the support frame 232 so as to permit the eye movements of the user to be detected in darkness. As such, the light-proof cover enables the eye movements of the user to be recorded in complete darkness or nearly complete darkness. In one or more embodiments, the light-proof cover is in the form of a pull-down visor, such as that used on welding goggles. In one or more alternative embodiments, light-proof cover is in the form of a snap-on cover that snaps around the support frame 232, and in front of the dichroic mirrors 224, 226.

Figure 8:
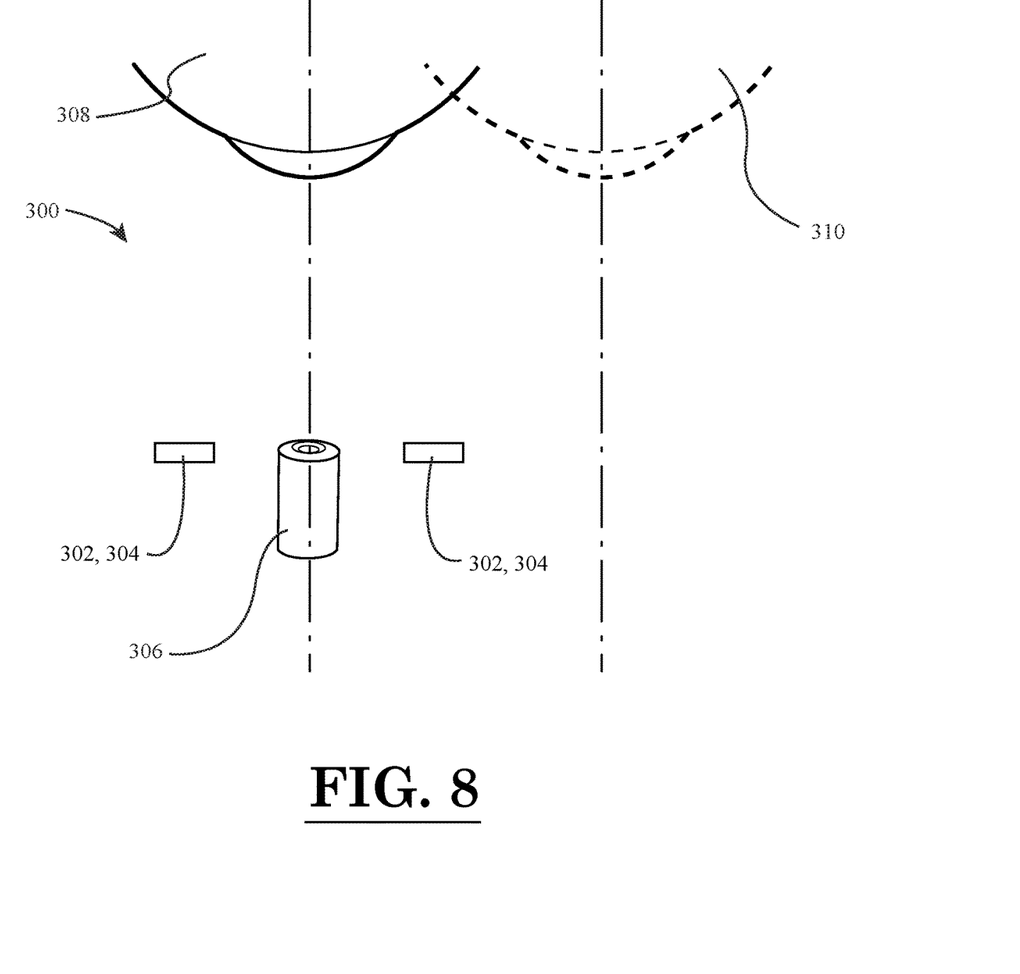
FIG. 8 is a schematic diagram illustrating the manner in which a video-based sensor is capable of being used for the alignment of non-video-based sensors.
Figure 9:
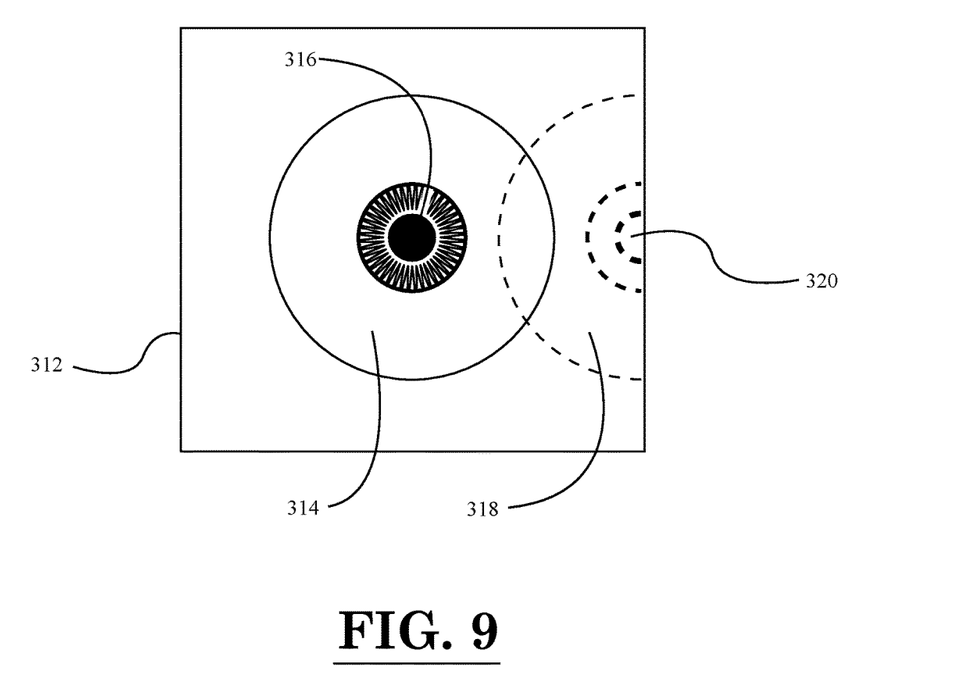
FIG. 9 depicts an example alignment of an eye using an image captured by the video-based sensor of FIG. 8.

In addition, in one or more further embodiments, the non-video-based sensors (e.g., infrared sensors) may be located relative to the optical of axis of the video-based sensor(s) (e.g., a camera) according to a known relationship (e.g., a predetermined distance or distances between the sensors, etc.) so as to enable the video-based sensor(s) to be used for the alignment of the non-video-based sensors. For example, as shown in the schematic diagram 300 of FIG. 8, non-video-based sensors 302, 304 are arranged on opposite sides of the video-based sensor 306, which may be in the form of a camera 306. More specifically, the non-video-based sensors 302, 304 are spaced apart from the camera optical axis (as indicated by the centerline in FIG. 8) by known horizontal distances. In FIG. 8, the actual position of the eye 310 is shown offset to the right of the optical axis of the camera 306. As shown in FIG. 8, the desired position of the eye 308 is centered on the camera optical axis. Because a known fixed relationship exists between the location of the camera 306 and the non-video-based sensors 302, 304 in FIG. 8, the non-video-based sensors 302, 304 may be aligned in accordance with the actual position of the eye 310 by using the image information obtained from the camera 306. For example, FIG. 9 depicts an example alignment of an eye using an image 312 captured by the camera 306 in FIG. 8. In FIG. 9, the eye 318 with pupil 320 depicts the actual location of the eye as captured by the camera 306, while the centered eye 314 with pupil 316 depicts the desired position of the eye in the image. The offset distance between the eye 318 and the eye 314 in FIG. 9 may be used to adjust the non-video-based sensors 302, 304 of FIG. 8 to account for the non-centered position of the eye 318.

Figure 10A:
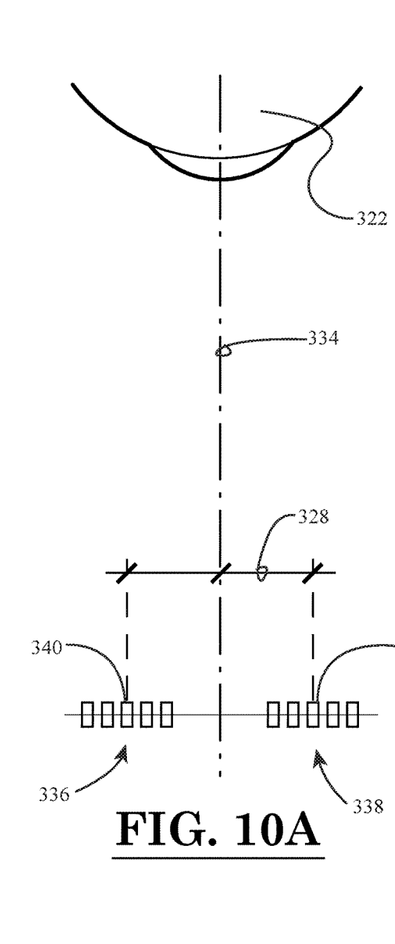
FIG. 10A is a schematic diagram depicting an eye that is centered with respect to two sets of non-video-based sensors.
Figure 11A:
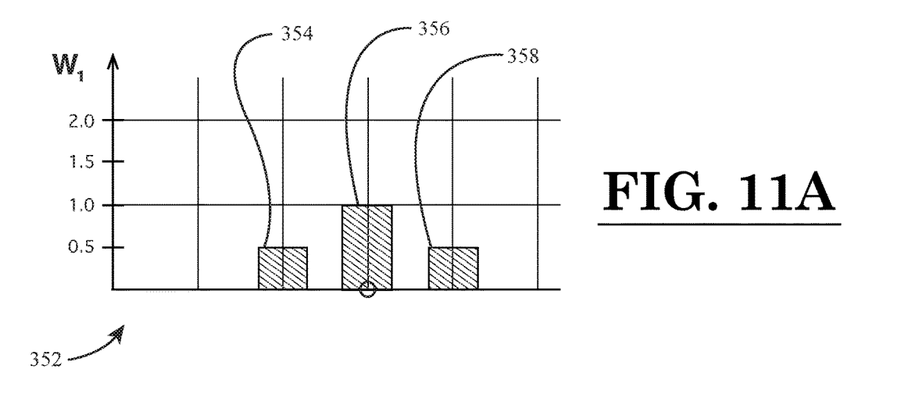
FIG. 11A is a first bar graph illustrating numerical weights applied to the sensor output values of the non-video-based sensors in FIG. 10A.

Next, referring to FIGS. 10A-10C and 11A-11C, an exemplary manner in which the non-video-based sensors may be calibrated so as to compensate for the misalignment of an eye relative to the non-video-based sensors will be described. Initially, as shown in FIG. 10A, the central axis 334 of the eye 322 is shown centered on, and bisecting the dimensional line 328 extending from the center location of the first set of non-video-based sensors 336 to the center location of the second set of non-video-based sensors 338. Because the eye 322 is centered relative to both sets of non-video-based sensors 336, 338 in FIG. 10A, a weight of 1.0 is applied to the centermost sensors 340, 342 of each non-video-based sensor set 336, 338, while a weight of 0.5 is applied to the two sensors disposed on opposite sides of the centermost sensors 340, 342. The weighting of the non-video-based sensors 336, 338 is graphically illustrated in the bar graph 352 of FIG. 11A. As shown in FIG. 11A, the weights of 1.0 that are applied to the centermost sensors 340, 342 are represented by the center bar 356, while the weights of 0.5 that are applied to the two sensors disposed on opposite sides of the centermost sensors 340, 342 are represented by the bars 354, 358.

Figure 10B:
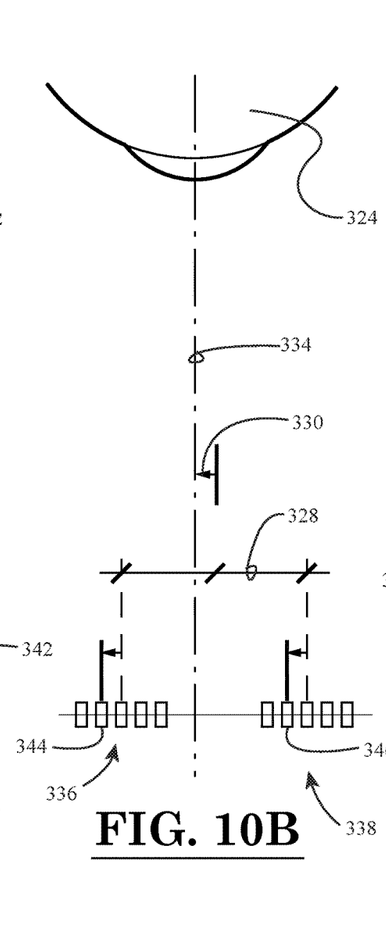
FIG. 10B is a schematic diagram depicting an eye that is displaced to the left by a first distance relative to two sets of non-video-based sensors.
Figure 11B:
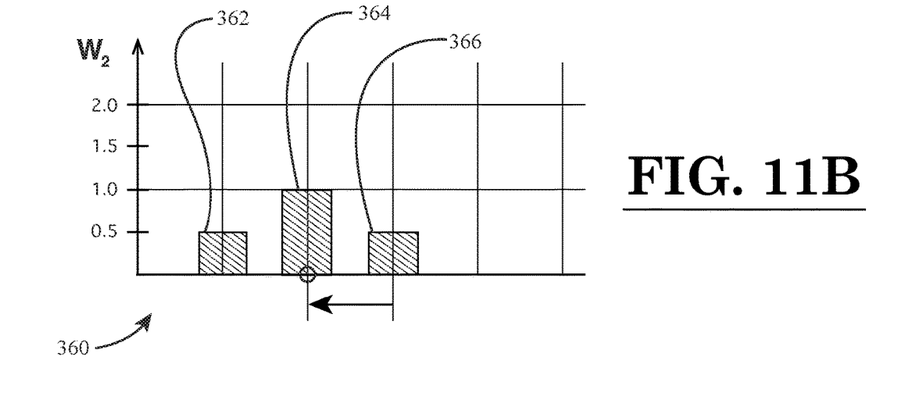
FIG. 11B is a second bar graph illustrating numerical weights applied to the sensor output values of the non-video-based sensors in FIG. 10B.

Turning FIG. 10B, the central axis 334 of the eye 324 is shown offset to the left of the midpoint of the dimensional line 328 by a first distance 330. Because the eye 324 is misaligned to the left relative to both sets of non-video-based sensors 336, 338 in FIG. 10B, a weight of 1.0 is applied to the sensors 344, 346 of each non-video-based sensor set 336, 338, while a weight of 0.5 is applied to the two sensors disposed on opposite sides of the sensors 344, 346. The weighting of the non-video-based sensors 336, 338 is graphically illustrated in the bar graph 360 of FIG. 11B. As shown in FIG. 11B, the weights of 1.0 that are applied to the sensors 344, 346 are represented by the bar 364, while the weights of 0.5 that are applied to the two sensors disposed on opposite sides of the sensors 344, 346 are represented by the bars 362, 366.

Figure 10C:
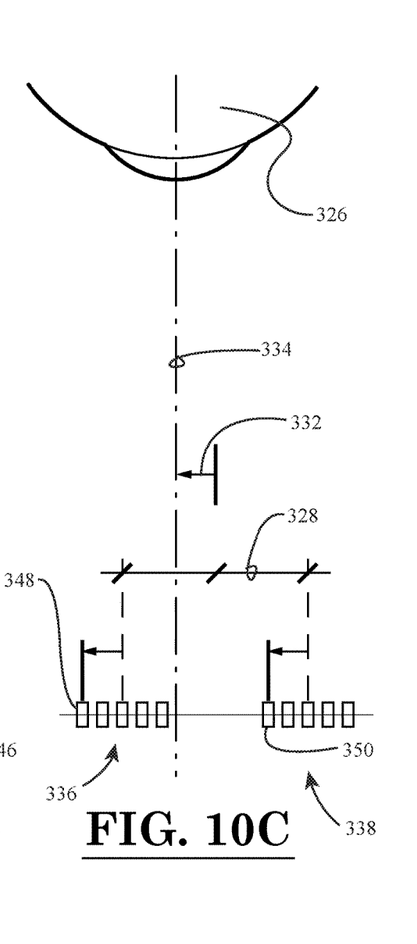
FIG. 10C is a schematic diagram depicting an eye that is displaced to the left by a second distance relative to two sets of non-video-based sensors, wherein the second distance of FIG. 10C is greater than the first distance of FIG. 10B.
Figure 11C:
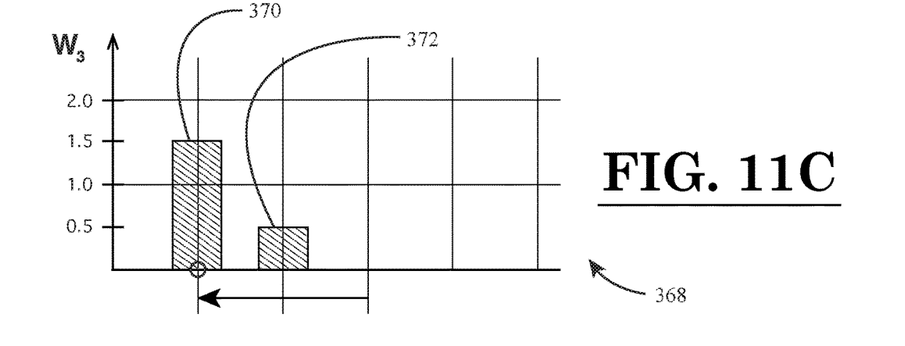
FIG. 11C is a third bar graph illustrating numerical weights applied to the sensor output values of the non-video-based sensors in FIG. 10C.

Next, as shown in FIG. 10C, the central axis 334 of the eye 326 is shown offset to the left of the midpoint of the dimensional line 328 by a second distance 332, which is greater than the offset distance 330 of FIG. 10B. Because the eye 326 is misaligned to the left relative to both sets of non-video-based sensors 336, 338 in FIG. 10C by a greater distance than that of FIG. 10B, a weight of 1.5 is applied to the leftmost sensors 348, 350 of each non-video-based sensor set 336, 338, while a weight of 0.5 is applied to the sensors disposed on right sides of the sensors 348, 350. The weighting of the non-video-based sensors 336, 338 is graphically illustrated in the bar graph 368 of FIG. 11C. As shown in FIG. 11C, the weights of 1.5 that are applied to the sensors 348, 350 are represented by the bar 370, while the weights of 0.5 that are applied to the sensors disposed on right sides of the sensors 348, 350 are represented by the bar 372.

In the embodiment of FIGS. 10A-10C and 11A-11C, the misalignment of the eye relative to the non-video-based sensors is compensated for by selectively applying weights to particular sensors in sensor sets. Although, in other embodiments, the misalignment of the eye relative to the non-video-based sensors may be compensated for by translating and/or rotating the non-video-based sensors using actuators based upon the information obtained from the video-based sensor(s).

Referring again to FIG. 3, it can be seen that, in the illustrative embodiment, the eye movement measurement device 200 further comprises a target generation device (e.g., a target light source 208) mounted on the support frame 232. The target generation device 208 is configured to generate a target and project the target onto a surface (e.g., a wall surface) in front of the user such that the target is visible by the eyes 10, 20 of the user. The target generation device 208 may be in the form of a laser light source or a light emitting diode.

In addition, in one or more embodiments, the eye movement measurement device 200 further comprises a data storage device mounted on the support frame 232. The data storage device comprises non-volatile data storage means, and is configured to store eye movement data so as to enable the eye movement data to be subsequently downloaded to a remote computing device.

The data processing device 136 of the eye movement measurement device 200 is the same as that described above for the first embodiment. In the illustrative embodiment, the data processing device 136 is operatively coupled to the light sources 210, 212, 214, 216, the pair of video-based sensors 202, 204, the pair of non-video-based sensors 218, 220, the target light source 208 and the head position detection device 244 by means of a wireless connection. In an alternative embodiment, the data processing device 136 may be operatively coupled to the light sources 210, 212, 214, 216, the pair of video-based sensors 202, 204, the pair of non-video-based sensors 218, 220, the target light source 208 and the head position detection device 144 by means of a hardwired connection.

In the illustrative embodiment, the eye movement measurement devices 100, 200 are configured to determine the gaze direction of a subject. Once the subject has been outfitted with the eye movement measurement device 100, 200, the eye movement of the subject is determined based upon the output data from the video-based sensors 102, 104, 202, 204 and the non-video-based sensors 118, 120, 218, 220 of the eye movement tracking device 100, 200, while the head position of the subject is determined based upon the output data from the head position detection device 144. The gaze direction of the subject is generally equal to the sum of the head movement and the eye movement, and is given in degrees per second.

The eye movement measurement devices 100, 200 described above may be used for a variety of different eye tests. For example, the eye movement measurement devices 100, 200 may be used in head impulse testing in which the subject's head is moved rapidly either in the horizontal or vertical planes. The examining clinician or physician stands behind the subject while holding the head. The subject is instructed to stare at a stationary dot placed about one meter straight ahead. During several rapid head movements either horizontally (right-left) or vertically (up-down), the eye and head velocities will be determined by the device and used to quantify the performance of the semicircular canals within the vestibular system.

While reference is made throughout this disclosure to, for example, "one embodiment" or a "further embodiment", it is to be understood that some or all aspects of these various embodiments may be combined with one another as part of an overall embodiment of the invention. That is, any of the features or attributes of the aforedescribed embodiments may be used in combination with any of the other features and attributes of the aforedescribed embodiments as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. An eye movement measurement device, comprising:
at least one light source configured to illuminate one or more eyes of a user;
at least one video-based sensor configured to detect low speed eye movements of the one or more eyes of the user and output one or more first signals based upon the detected low speed eye movements;
at least one non-video-based sensor configured to detect high speed eye movements of the one or more eyes of the user and output one or more second signals based upon the detected high speed eye movements; and
a data processing device operatively coupled to the at least one light source, the at least one video-based sensor, and the at least one non-video-based sensor, the data processing device configured to receive the one or more first signals that are generated based upon the detected low speed eye movements and the one or more second signals that are generated based upon the detected high speed eye movements, and to calculate one or more eye movement output values for the one or more eyes of the user based upon the one or more first signals and the one or more second signals.

2. The eye movement measurement device according to claim 1, wherein the at least one light source comprises one or more light emitting diodes configured to illuminate the one or more eyes of the user, and wherein the data processing device is configured to activate the one or more light emitting diodes.

3. The eye movement measurement device according to claim 1, wherein the at least one video-based sensor comprises one or more video cameras, and wherein the at least one non-video-based sensor is selected from the group consisting of an infrared sensor, an ultrasound sensor, an electooculographic sensor, and combinations thereof.

4. The eye movement measurement device according to claim 1, further comprising a dichroic mirror disposed in a path of a reflected image of one of the one or more eyes of the user between the one of the one or more eyes of the user and the at least one video-based sensor.

5. The eye movement measurement device according to claim 1, further comprising a head position detection device, the head position detection device configured to detect a position of the head of the user and output one or more third signals that are representative of the detected position of the head of the user, wherein the head position detection device comprises one or more inertial measurement units.

6. The eye movement measurement device according to claim 1, further comprising a support frame on which the at least one light source, the at least one video-based sensor, and the at least one non-video-based sensor are mounted, the support frame configured to be worn on the head of the user, wherein the support frame is in the form of a pair of goggles.

7. The eye movement measurement device according to claim 6, further comprising a frame slippage detection device, the frame slippage detection device configured to detect a slippage of the support frame relative to the head of the user.

8. The eye movement measurement device according to claim 7, wherein the frame slippage detection device comprises one or more video cameras.

9. The eye movement measurement device according to claim 6, further comprising a light-proof cover mounted on the support frame, the light-proof cover configured to at least partially surround a front of the support frame so as to permit the eye movements of the user to be detected in darkness.

10. The eye movement measurement device according to claim 6, further comprising a target generation device mounted on the support frame, the target generation device configured to generate a target and project the target onto a surface in front of the user such that the target is visible by the one or more eyes of the user, wherein the target generation device is in the form of a laser light source or a light emitting diode.

11. The eye movement measurement device according to claim 6, further comprising a data storage device mounted on the support frame, the data storage device comprising non-volatile data storage means, and the data storage device configured to store eye movement data from the data processing device so as to enable the eye movement data to be subsequently downloaded to a remote computing device.

12. An eye movement measurement device, comprising:
a support frame configured to be worn on the head of a user;
at least one light source mounted on the support frame, the at least one light source configured to illuminate one or more eyes of the user;
at least one video-based sensor mounted on the support frame, the at least one video-based sensor configured to detect low speed eye movements of the one or more eyes of the user and output one or more first signals based upon the detected low speed eye movements;
at least one non-video-based sensor mounted on the support frame, the at least one non-video-based sensor configured to detect high speed eye movements of the one or more eyes of the user and output one or more second signals based upon the detected high speed eye movements;
a head position detection device, the head position detection device configured to detect a position of the head of the user and output one or more third signals that are representative of the detected position of the head of the user; and
a data processing device operatively coupled to the at least one light source, the at least one video-based sensor, the at least one non-video-based sensor, and the head position detection device, the data processing device configured to receive the one or more first signals that are generated based upon the detected low speed eye movements, the one or more second signals that are generated based upon the detected high speed eye movements, and the one or more third signals that are generated based upon the detected position of the head of the user, and the data processing device configured to determine one or more gaze directions of the user from the one or more first signals output by the at least one video-based sensor, the one or more second signals output by the at least one non-video-based sensor, and the one or more third signals output by the head position detection device.

13. The eye movement measurement device according to claim 12, wherein the at least one light source comprises one or more light emitting diodes configured to illuminate the one or more eyes of the user, and wherein the data processing device is configured to activate the one or more light emitting diodes.

14. The eye movement measurement device according to claim 12, wherein the at least one video-based sensor comprises one or more video cameras, and wherein the at least one non-video-based sensor is selected from the group consisting of an infrared sensor, an ultrasound sensor, an electooculographic sensor, and combinations thereof.

15. The eye movement measurement device according to claim 12, further comprising a dichroic mirror disposed in a path of a reflected image of one of the one or more eyes of the user between the one of the one or more eyes of the user and the at least one video-based sensor.

16. The eye movement measurement device according to claim 12, wherein the head position detection device comprises one or more inertial measurement units.

17. The eye movement measurement device according to claim 12, wherein the support frame is in the form of a pair of goggles.

18. The eye movement measurement device according to claim 12, further comprising a frame slippage detection device, the frame slippage detection device configured to detect a slippage of the support frame relative to the head of the user, wherein the frame slippage detection device comprises one or more video cameras.

19. The eye movement measurement device according to claim 12, further comprising a light-proof cover mounted on the support frame, the light-proof cover configured to at least partially surround a front of the support frame so as to permit the eye movements of the user to be detected in darkness.

20. The eye movement measurement device according to claim 12, further comprising a target generation device mounted on the support frame, the target generation device configured to generate a target and project the target onto a surface in front of the user such that the target is visible by the one or more eyes of a user, wherein the target generation device is in the form of a laser light source or a light emitting diode.

* * * * *